(12) United States Patent
Binder

(10) Patent No.: US 11,877,923 B2
(45) Date of Patent: Jan. 23, 2024

(54) SELF-ACCOMODATING LENS AND METHOD FOR CONTROLLING A SELF-ACCOMODATING LENS

(71) Applicant: Helmut Binder, Berlin (DE)

(72) Inventor: Helmut Binder, Berlin (DE)

( * ) Notice: Subject to any disclaimer, the term of this patent is extended or adjusted under 35 U.S.C. 154(b) by 18 days.

(21) Appl. No.: 17/454,089

(22) Filed: Nov. 9, 2021

(65) Prior Publication Data

US 2022/0142769 A1    May 12, 2022

(30) Foreign Application Priority Data

Nov. 11, 2020    (DE) .................... 10 2020 129 721.1

(51) Int. Cl.

| A61F 2/16 | (2006.01) |
|---|---|
| A61F 2/48 | (2006.01) |
| G02C 7/04 | (2006.01) |
| G02C 7/08 | (2006.01) |
| H01Q 1/27 | (2006.01) |
| H01Q 9/04 | (2006.01) |
| H01Q 21/20 | (2006.01) |

(52) U.S. Cl.
CPC ............ *A61F 2/1635* (2013.01); *A61F 2/482* (2021.08); *G02C 7/041* (2013.01); *G02C 7/081* (2013.01); *H01Q 1/273* (2013.01); *H01Q 9/0407* (2013.01); *H01Q 21/20* (2013.01); *A61F 2230/005* (2013.01); *A61F 2250/0001* (2013.01); *G02C 2202/06* (2013.01)

(58) Field of Classification Search
CPC .. A61F 2/1635; A61F 2/482; A61F 2230/005; A61F 2250/0001; G02C 7/041; G02C 7/081; G02C 2202/06; G02C 7/04; H01Q 1/273; H01Q 9/0407; H01Q 21/20
See application file for complete search history.

(56) References Cited

U.S. PATENT DOCUMENTS

| 8,636,358 B2 | 1/2014 | Binder |
| 9,450,304 B1* | 9/2016 | Edalati ................ H01Q 1/246 |
| 2008/0306589 A1 | 12/2008 | Donitzky et al. |
| 2010/0103368 A1 | 4/2010 | Amirparviz et al. |
| 2012/0092612 A1* | 4/2012 | Binder .................. G02C 7/081 |
| | | 351/159.02 |

(Continued)

FOREIGN PATENT DOCUMENTS

| DE | 102015000248 A1 | 7/2016 |
| EP | 1726272 A1 | 11/2006 |

(Continued)

OTHER PUBLICATIONS

Definition of MEMS, retrieved from https://www.mems-exchange.org/MEMS/what-is.html (Year: 2023).*

(Continued)

*Primary Examiner* — Megan Y Wolf
*Assistant Examiner* — Yasniary De La Caridad Morales

(57) ABSTRACT

The disclosure relates to a self-accommodating lens, which is formed in particular as a contact lens. The lens includes a lens body configured to be placed onto or into an eye of a patient. A plurality of actuators are arranged in a star-shaped manner on the front side of the lens body. The angle to an adjacent lens is determined by detection of a directional radio signal.

8 Claims, 9 Drawing Sheets

(56) References Cited

U.S. PATENT DOCUMENTS

| | | | |
|---|---|---|---|
| 2012/0140167 A1* | 6/2012 | Blum | G02C 7/04 |
| | | | 351/159.73 |
| 2014/0243971 A1 | 8/2014 | Pugh et al. | |
| 2016/0081793 A1 | 3/2016 | Galstian et al. | |
| 2017/0367815 A1* | 12/2017 | Basinger | A61F 2/1635 |
| 2018/0055626 A1* | 3/2018 | Beer | A61F 2/1629 |
| 2018/0129070 A1 | 5/2018 | Fryers et al. | |
| 2018/0129072 A1* | 5/2018 | Aschwanden | B29D 11/0023 |
| 2019/0028159 A1* | 1/2019 | Bisiules | H01Q 5/48 |

FOREIGN PATENT DOCUMENTS

| | | | | |
|---|---|---|---|---|
| EP | 2772791 B1 | 3/2020 | | |
| WO | 2010004094 A1 | 1/2010 | | |
| WO | WO-2019177540 A1 * | 9/2019 | | A61B 3/10 |

OTHER PUBLICATIONS

Definition of actuator, retrieved from https://www.merriam-webster.com/dictionary/actuator (Year: 2023).*

* cited by examiner

SELF-ACCOMODATING LENS AND METHOD FOR CONTROLLING A SELF-ACCOMODATING LENS

CROSS-REFERENCE TO RELATED APPLICATION

This application claims the benefit of German Patent Application No. 10 2020 129 721.1, filed Nov. 11, 2020, the contents of which is hereby incorporated by reference in its entirety.

TECHNICAL FIELD

The disclosure relates to a self-accommodating lens. The lens is formed in particular as a contact lens. The disclosure further relates to a method for controlling a self-accommodating lens.

BACKGROUND

Self-accommodating lenses are lenses which can change their focal length. Such lenses are generally known.

For instance, the published patent application WO 2010/133317 A1 (Dr. Helmut Binder) describes a self-accommodating lens comprising a position sensor.

According to the teaching of this published patent application, the angle of the optical axes between two lenses is measured, and the curvature of the lens is changed on the basis of the measured angle, in order to adapt the focal length to the distance in this way.

In contrast to contact lenses which have ring segments comprising a different focal length, a self-accommodating contact lens has the advantage that the entire image depicted on the retina originates from a single lens comprising an essentially uniform focal length. Further, there are no contrast losses and also no interfering scattering effects.

This makes it easier for the user to get used to the contact lens, and the light intensity of the eye is furthermore retained completely.

It is desirable that self-accommodating contact lenses are used in particular in the case of presbyopia or in connection with a non-accommodating intraocular lens after a cataract surgery.

However, the technical implementation of such a system is difficult. The integration of the required components for the angle measurement as well as the change of the curvature of the lens is particularly difficult.

SUMMARY

The disclosure is based on the object of improving the integration of a mechanical system for changing the radius of curvature of a lens and thus of the refractive index and/or the measurement of the angle between two adjacent lenses.

The object is achieved by a self-accommodating lens as well as by a method for controlling a self-accommodating lens according to any one of the independent claims.

Preferred embodiments and further developments can be gathered from the subject matter of the dependent claims, the description, as well as the drawings.

According to a first aspect, the disclosure relates to a self-accommodating lens.

The lens is formed in particular as a contact lens, thus as a lens, which is placed onto the cornea and attaches itself there.

On principle, however, the disclosure can also be used for an intraocular lens, thus a lens, which is formed as implant for replacing the human lens.

The lens comprises a lens body, which is at least partially formed of a transparent elastic material.

The lens can in particular be formed of a silicon, in particular of a silicon hydrogel.

The material of the lens can be deformed in order to thus change the focal length as a function of the distance to the object, at which the user of the lens looks.

The lens comprises a lens body comprising a front side and a rear side. The rear side is the side facing the user, thus the proximal side, whereas the front side represents the side facing away from the user, thus the distal side, which, in the case of a contact lens, is in particular formed as outer side.

At least one actuator for changing the curvature of the lens is arranged on the front side of the lens.

It has been found that a change of the refractive index is already possible in a simple manner by means of the change of the curvature of the lens, starting at the front side thereof.

In the case of an elastic body, the curvature of the front side is further changed more strongly than on the rear side by means of the actuator, which is present on the front side.

The rear side, which can be adapted to the curvature of the eye, changes less or not at all when changing the focal length.

As a result, the change of the focal length of a self-accommodating contact lens is not noticeable for the wearer or only slightly noticeable for the wearer.

The arrangement of the at least one actuator on the front side is understood such that the actuator is arranged in such a way that it directly changes the curvature on the front side, in particular the outer side of a contact lens.

The actuator can thereby form the outer side of the lens during intended use.

The actuator or the actuators can further be provided with a transparent layer, in particular made of the same material as the remaining lens body.

The lens preferably comprises a plurality of actuators.

The lens can comprise 2 to 20, preferably 4 to 16, and most preferably 6 to 12 actuators.

The actuators are preferably formed in a strip-shaped manner and change their curvature as a function of a control signal.

The actuators in particular extend over the front side of the lens in a star-shaped manner.

The curvature of the lens can be changed in a very simple manner via micromechanical components attached to the front side.

The actuators can extend over the front side of the lens in particular in a star-shaped manner.

In the case of suitably small actuators, it is also possible thereby that the actuators contact and/or overlap one another in the optical center of the lens.

In particular strip-shaped actuators can thus be distributed in a star-shaped manner, starting at the center, thus at the optical center.

In the case of another embodiment, the actuators are arranged around a recessed central region, in particular around a circular central region.

This embodiment does have the disadvantage that the curvature of the lens and thus the change of the refractive index can be changed with less efficiency.

At the same time, however, the optical center is free from actuators.

According to a preferred embodiment, the accommodating lens is formed in such a way that the curvature can be adjusted step by step, in particular in 2 to 5 steps, preferably in exactly 3 steps.

It has been shown that a stepless accommodation is not necessary. On the contrary, few, firmly defined, different focal lengths are already sufficient in order to perform a sufficient accommodation over the entire viewing area.

The step by step change of the focal length provides for an activation, which is simpler from a control-related aspect, of the actuators.

This applies in particular in connection with a directional radio signal, to which a further aspect of the disclosure refers.

This is so because only the exceeding or falling below, respectively, of threshold values has to also be detected by measurement, but the angle of the optical axes does not need to be calculated continuously.

The lens can thus be operated in a more energy-saving manner.

This applies in particular for an embodiment, in the case of which the lens is formed in such a way that, in a far vision stage, said lens comprises actuators, which are in their rest position.

The actuators have to be activated by a control unit only when the user no longer positions his eyes to far vision, and only then is corresponding energy required for this.

The actuator can in particular be formed as micro-electromechanical system (MEMS).

Actuators of this type can in particular operate according to the electrostatic principle.

The at least one actuator can thus in particular comprise a flexible substrate, which can in particular also be part of the lens body.

An actuator of this type can change its curvature in a simple manner via electrodes located opposite one another, between which a hollow space is arranged in the substrate.

Being arranged on the front side of the lens, the curvature of the lens is thus also changed, so that the focal length can be changed.

An angle to another lens is preferably used as input variable for the actuator.

It goes without saying that the angle correlates with the distance in the center point of the lens.

The angle can in particular be determined via a sensor.

The lens can further comprise an energy storage, in particular an energy storage, which is applied to the substrate, in particular to the lens body, in thin film technology.

The energy storage can in particular also be formed as multi-layer capacitor.

A so-called supercapacitor (supercap) can in particular be used as energy storage.

Said supercap can in particular be formed as double layer capacitor comprising carbon electrodes, as pseudo capacitor comprising electrodes made of metal oxides or of conductive polymers, or as so-called hybrid capacitor comprising asymmetrical electrodes.

According to a preferred embodiment, the lens can be charged inductively.

The induction coil required for this purpose can in particular extend concentrically over the front side of the lens.

According to a further aspect, the disclosure relates to a self-accommodating lens, in particular a contact lens and which can in particular have the above-described features.

The lens comprises a lens body, the curvature of which can be changed as a function of the angle to an adjacent lens.

As described above, the curvature can in particular be changed via at least one actuator.

The self-accommodating lens comprises an antenna, which emits a directional signal, for measuring the angle to the adjacent lens.

The directional signal, which can in particular also be defined as signal lobe, is detected by an opposite contact lens.

The angle can be detected on the basis of the signal intensity.

In the case of a gradual or step by step adjustment, respectively, of the curvature of the lens via an actuator, predefined threshold values can be used, in response to the falling below or exceeding of which, respectively, a control signal is changed at the actuator.

A hysteresis loop is preferably provided in a control-related manner around the threshold value, in order to prevent that the actuator is activated continuously with another signal around the threshold value.

In order to measure the signal intensity, the same antenna can be used, which simultaneously emits a directional radio signal in the direction of the other lens.

According to a further embodiment, the angle can further be determined in that several antennas are present, which are spaced apart from one another, whereby it is determined, on which antenna the radio signal is strongest.

In particular a step by step activation of the actuator can thus be performed.

According to a preferred embodiment, the antenna is formed as patch antenna.

Patch antennas of this type comprise a preferably rectangularly formed layer on a substrate.

In particular the lens body can serve as substrate.

The emission of a directional radio signal can be improved via the use of a patch array, thus a regular arrangement comprising a plurality of antennas.

Antenna reflectors are preferably provided behind the respective patches.

The patch antenna can in particular also be formed as curved patch array, which is applied to the lens in thin film technology.

The disclosure furthermore relates to a method for controlling the focal length of a self-accommodating lens, in particular as it has been described above.

The signal intensity of a directional radio signal of an adjacent lens is measured.

Based on the signal intensity of the radio signal, a control signal for at least one actuator, preferably a plurality of actuators, is calculated by means of a controller.

The at least one actuator or the actuators, respectively, is/are activated by means of the control signal to change the curvature of the lens.

The controller can in particular calculate the angle of the optical axis of two adjacent lenses and can thus activate the at least one actuator on the basis of the angle.

As described above, the control preferably takes place gradually, in particular at least in 2 stages and/or less than 10 stages, in particular in 2, 3, 4, or 5 stages.

As already specified above, a distance viewing stage is preferably present, in which the at least one actuator is in a rest position.

Current for activating the actuators is thus only required when the field of view moves in a near range.

This function similarly replicates the function of the human eye, in the case of which the sight muscle tenses in the near range.

The disclosure furthermore relates to a set comprising two self-accommodating lenses, which comprises at least one self-accommodating lens, as it has been described above.

The set preferably comprises two of the above-described lenses, each lens can in particular have a sender as well as a receiver.

The subject matter of the invention will be described in more detail below with reference to schematically illustrated exemplary embodiments on the basis of the drawings FIG. 1 to FIG. 11.

The following detailed description is merely exemplary in nature and is not intended to limit the invention or the application and uses of the invention. Furthermore, there is no intention to be bound by any theory presented in the preceding background or the following detailed description.

DETAILED DESCRIPTION

Figure 1:
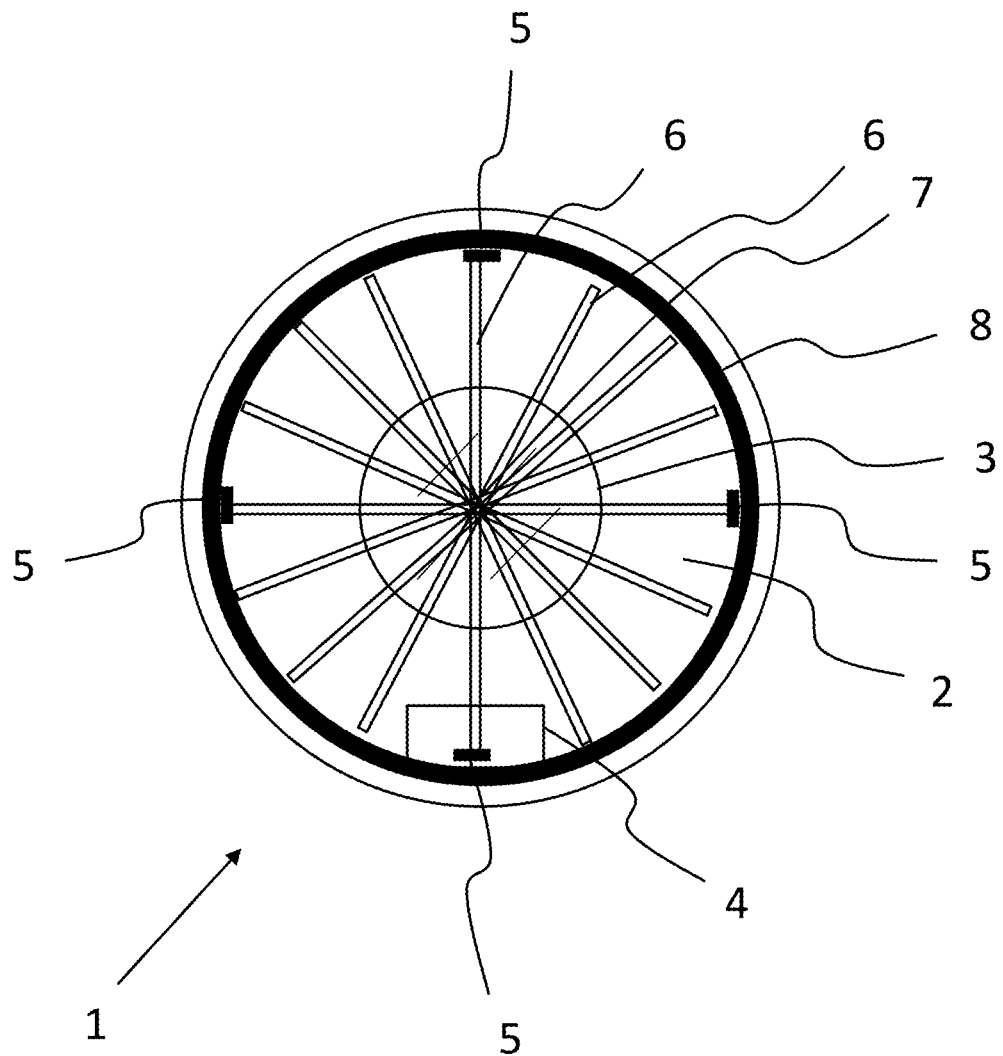
FIG. 1 and FIG. 2 show various exemplary embodiments of a self-accommodating lens, in each case in a schematic top view onto the front side.

FIG. 1 shows a self-accommodating lens 1 illustrated schematically in a top view onto the front side.

The self-accommodating lens 1 comprises a lens body 2 made of a transparent material, in particular a silicon.

When the lens 1 is placed into the human eye, a region 3 through which light falls into the eye when the iris is maximally opened, extends around a center point 7, on which the optical axis lies.

It goes without saying that the shape of the lens body 2 has to be changed in particular in this region, in order to attain another focal length.

For this purpose, the lens 1 comprises a plurality of actuators 6, which extend in a star-shaped manner virtually over the entire lens body 2.

The actuators 6 are attached to the front side of the lens body 2.

The actuators 6 are strip-shaped and can change the curvature of the front side of the lens 1.

In order to detect at what distance the eyes of the user (not illustrated) are focused, the angle to an adjacent lens 1 can be measured.

For this purpose, the lens can comprise a plurality of patch antennas 5, which are in particular formed as patch array.

The signal lobe of at least one patch antenna 5 can be detected and measured by an adjacent lens, as will be described in more detail below.

For the energy supply, the lens body 2 in this exemplary embodiment comprises a ring-shaped thin film battery 8, which extends concentrically around the actuators 6 in the outer region.

Conductor tracks for activating the actuators 6 as well as a coil for inductively charging the battery 8 can be arranged concentrically to the thin film actuator.

A controller 4 comprising the corresponding processors for the signal evaluation and activation of the actuators can be arranged on the front side of the lens body 2 or can be embedded in the lens body 2.

Figure 2:
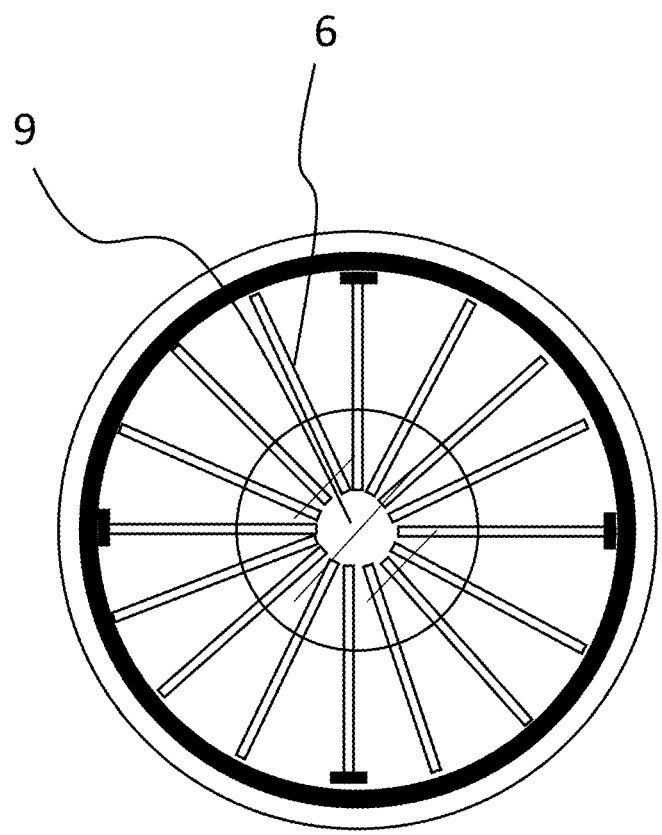

FIG. 2 shows an alternative exemplary embodiment.

In the case of this exemplary embodiment, the actuators 6 do not extend through the center point of the optical axis, but a free region 9 is provided, around which the actuators 6 extend radially.

Figure 3:
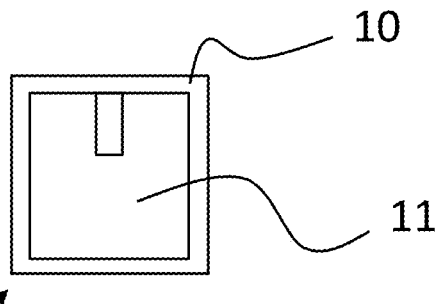
FIG. 3 is a detailed view of the antenna.
Figure 4:
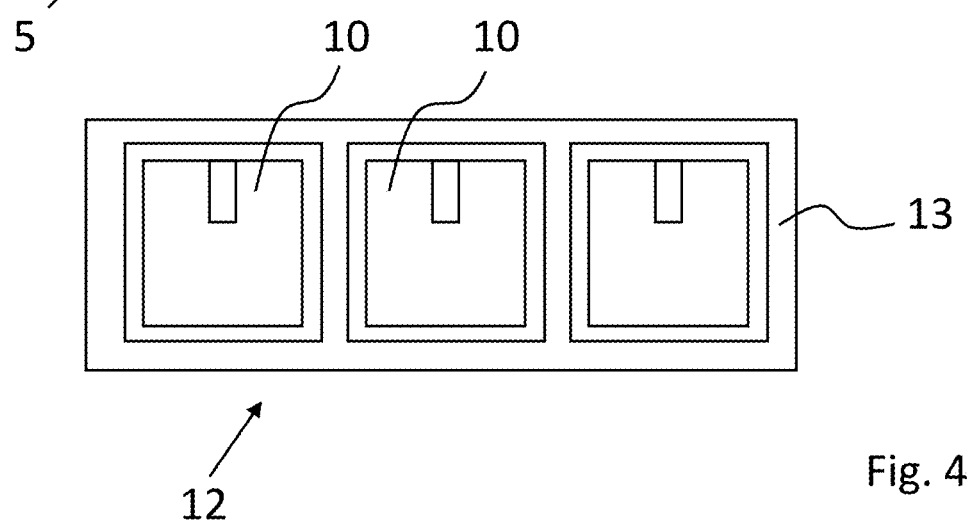
FIG. 4 shows a patch array.

FIG. 3 is a schematic view of a patch antenna 5.

The patch antenna comprises a rectangularly formed antenna 10, which is arranged on a reflector.

To attain a good directivity, a patch array 12 is preferably used, which comprises a plurality of antennas 10, which are arranged on a substrate 13.

Figure 5:
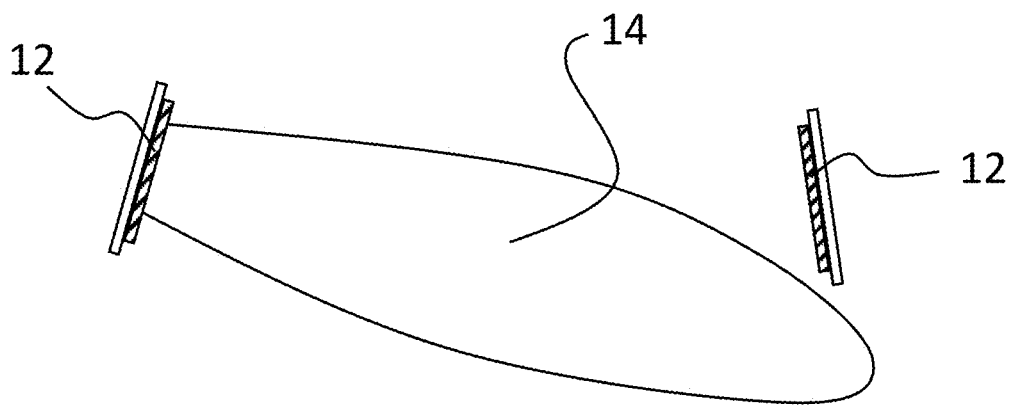
FIG. 5 is a symbolic illustration of the antenna during sending and receiving.

As illustrated schematically in FIG. 5, a signal lobe 14, which is detected by an opposite patch array 12, can be emitted via the patch array 12.

On the basis of the signal intensity, a conclusion can be drawn to the angle between the optical axes of the lens.

In this exemplary embodiment, only one antenna in the form of a patch array is in each case located on opposite sides.

In the case of another embodiment (not illustrated), several antennas are present, which are spaced apart from one another, and it is detected, at which antenna the signal lobe 14 is directed.

Figure 6:
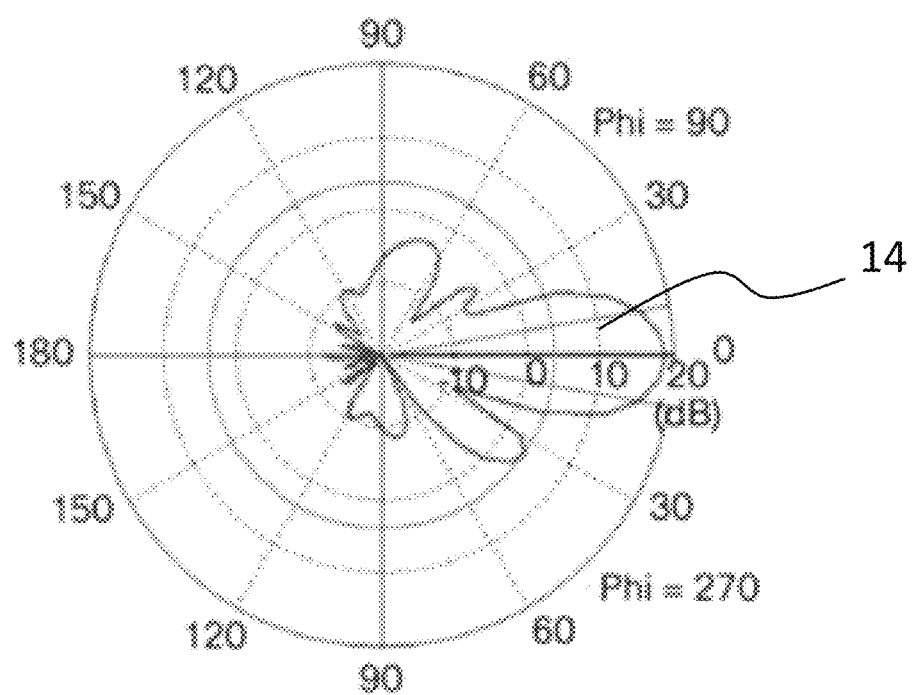
FIG. 6 is a simulation of the radio signal of an antenna, which is formed as patch array.

FIG. 6 shows the simulation of the signal lobe 14 of a patch array.

It can be seen that a patch array of this type has a good directivity. A portion with a high signal intensity in particular extends only over an angular range of approximately 30°.

Figure 7:
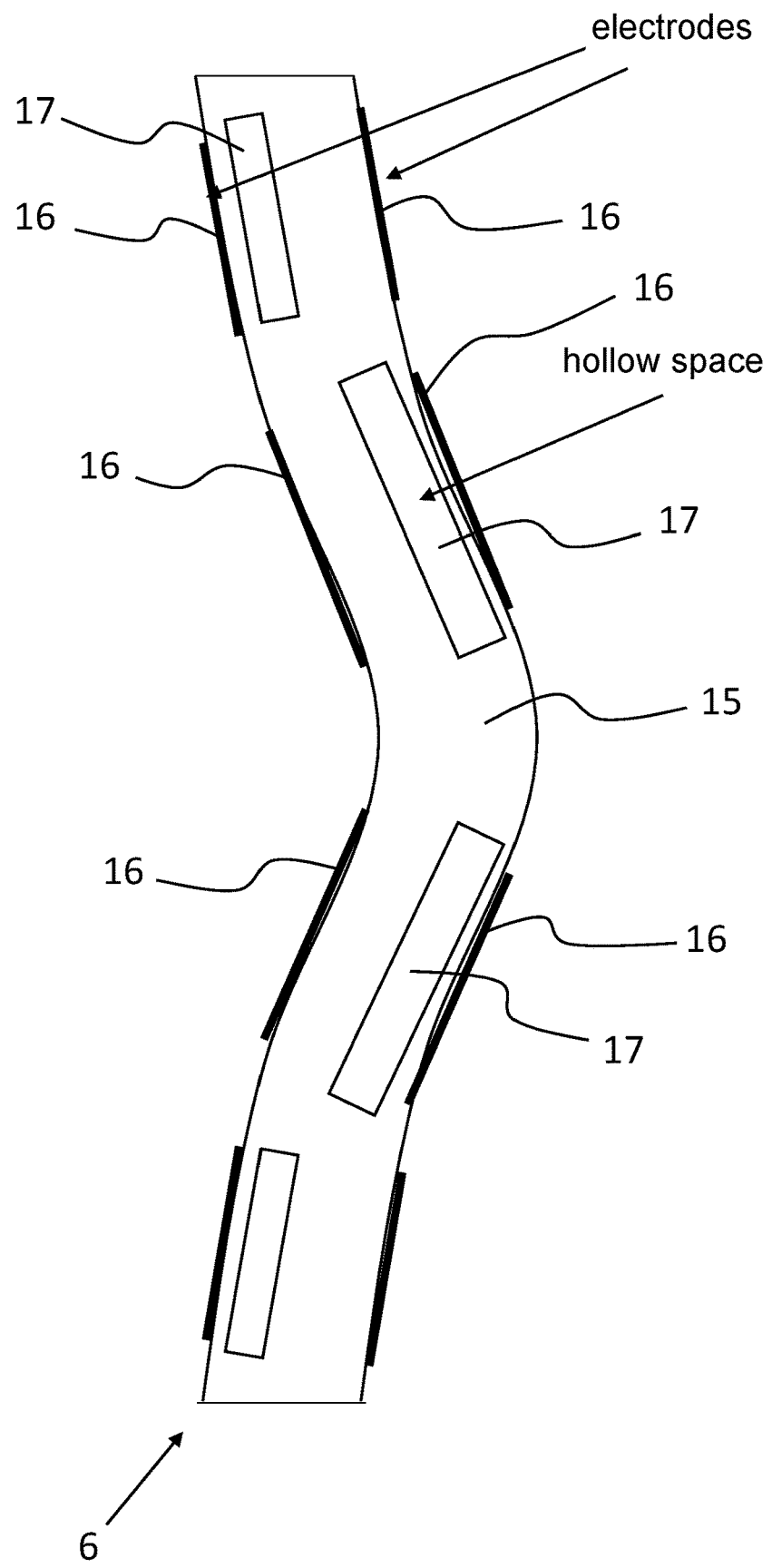
FIG. 7 schematically shows an electrostatic actuator.

FIG. 7 shows the basic principle of an exemplary embodiment of an actuator used for the self-accomodating lens in a schematic side view.

The actuator comprises a flexible substrate 15.

Said flexible substrate is preferably formed in a strip-shaped manner and can also be part of the lens body.

A plurality of electrode pairs 16 located opposite one another are arranged on front and rear side of the substrate 15.

A hollow space 17 is in each case located between the electrode pairs 16.

The hollow space 17 preferably extends in a strip-shaped manner and parallel along the electrodes 16.

The curvature of the substrate 15 can be changed on electrostatic basis via the position of the hollow space 17 and the activation of the electrodes 16.

The rest state, thus the state when no voltage is applied to the electrodes 16, is shown in this schematic exemplary embodiment.

The flexible substrate 15 thereby follows the basic contour of the lens body.

If a voltage is now applied, the hollow spaces 17 can be pushed together or pulled apart transversely to their main direction of extension, which has the result that the curvature of the flexible substrate 15 and thus the curvature on the top side of the lens body changes.

A change of the top side of the lens body is associated with a contour change with respect to the convexity as a whole, and thus changes the focal length of the lens.

Figure 8:
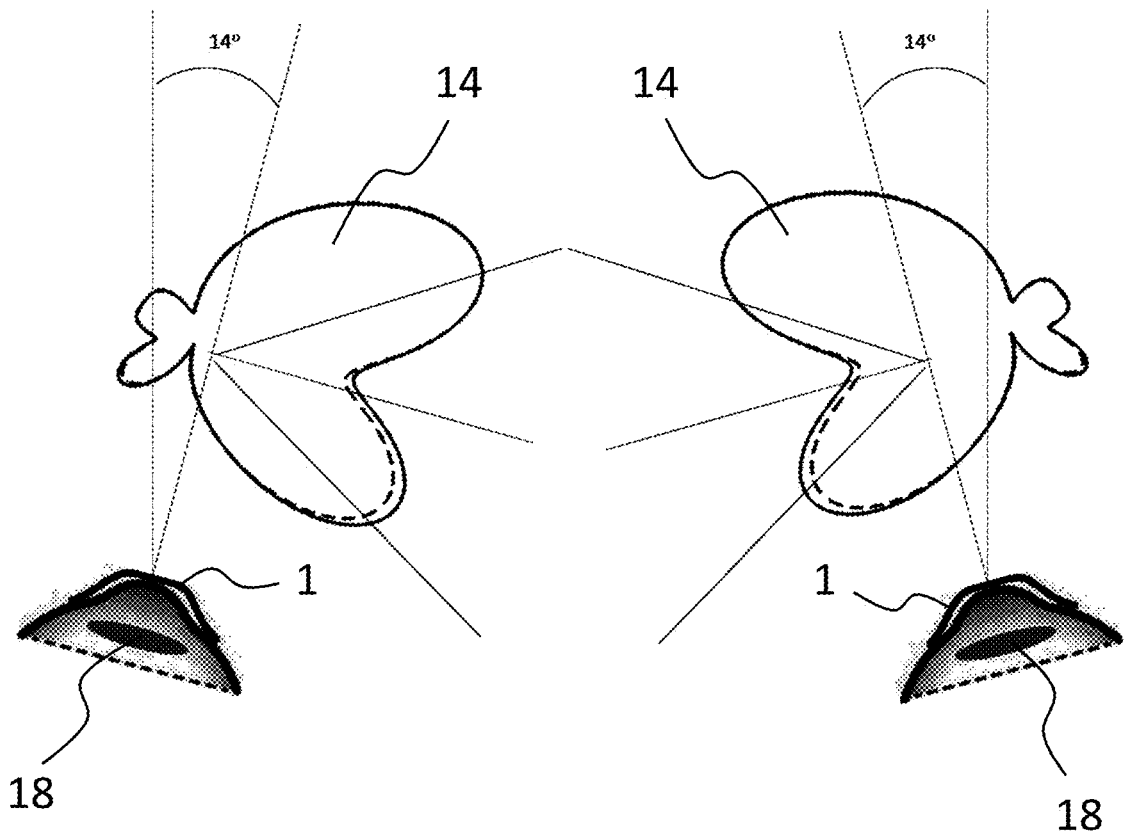
FIG. 8 is an illustration of the eyes of the user comprising two self-accommodating lenses.

The functional principle of the disclosure is illustrated schematically in FIG. 8.

The two eyes 18 of the user are illustrated, which are located opposite one another and which are focused on the near range here in slightly exaggerated illustrated.

The eyes 18 thus extend inwardly at a relatively large angle.

The user wears two contact lenses 1 according to the disclosure.

It can be seen that the schematically illustrated radio lobes 14 radiate in a different direction, depending on the angle of the eyes 18.

Figure 9:
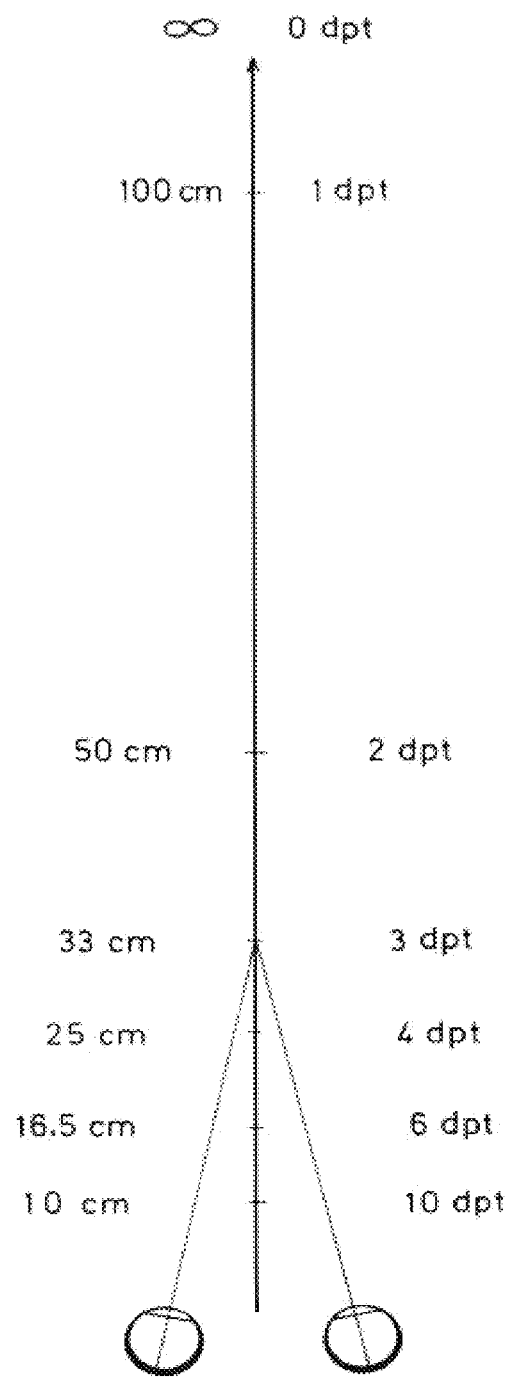
FIG. 9 shows the connection of the distance of an object and the diopter required for this.

FIG. 9 shows the connection between near vision and far vision and the diopter required for this.

In the case of a healthy person with normal eyesight, the lens of the human eye is also set to far vision to a rest position.

If the lens cannot deform any longer or also after a cataract surgery, an adaptation of the diopter is necessary for the near field of view, which starts at approximately 1 m.

It goes without saying that the diopter of up to 10 cm illustrated here is not necessary.

Figure 10:
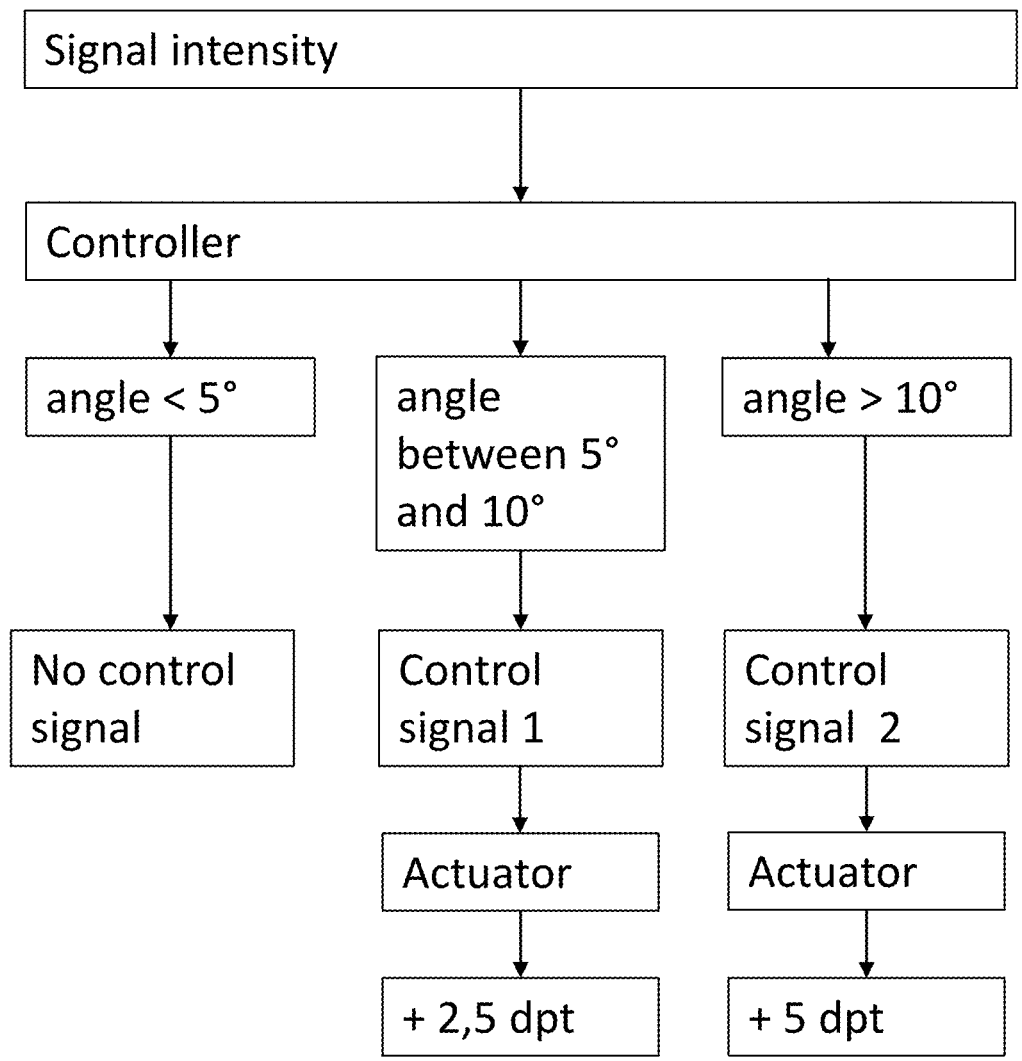
FIG. 10 is a flowchart of an exemplary embodiment of the method for controlling a self-accommodating lens.

An exemplary embodiment of the method for controlling a lens, in particular a contact lens, is illustrated in FIG. 10.

The signal intensity of the radio lobe of the adjacent lens is measured by means of an antenna, in particular by means of a patch antenna.

It is now determined via a controller, at what angle the eyes are inclined relative to the optical axis.

An angle of less than 5° suggests that the eyes of the user are set to far vision, for example because the user focusses on an object in the distance.

The actuators thereby remain in the rest position and no control signal is emitted to the actuators via the controller.

When changing into the near field, the actuators can be changed in two stages.

In the case of an angle of between 5° and 10°, the focal length is changed via a first control signal by activation of the actuators in such a way that the diopter increases by 2.5.

In the case of an angle of 10°, the controller switches to maximum near vision, and a second control signal is generated, by means of which the actuators increase the diopter by 5.

A modulation of this type in three stages is already sufficient in order to be able to focus on objects in the distance sharply as well as to be able to work in front of a monitor in the near vision range and in order to be able to read normal text size, without additional visual aid.

Figure 11:
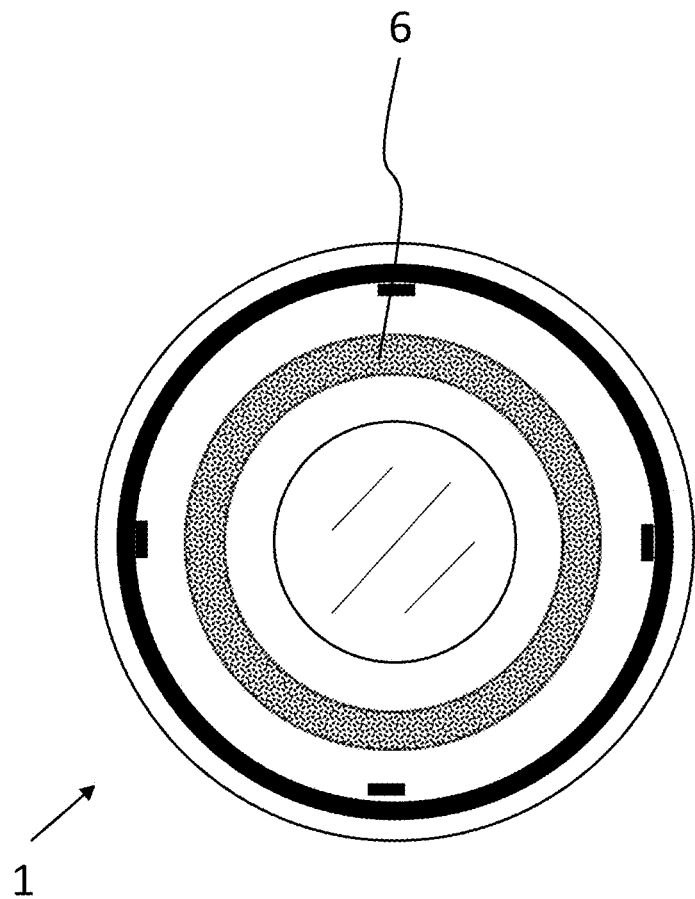
FIG. 11 is a schematic illustration of a further embodiment of a self-accommodating lens.

FIG. 11 shows a further embodiment of a self-accommodating lens 1 in a schematic illustration.

In the case of this embodiment, the actuator 6 is formed as a concentric ring.

Said concentric ring can comprise electroactive polymers, such as, e.g., polypyrrole, which, due to a volume change due to an electrochemical oxidation and reduction by applying a low voltage of less than 3V, contract the actuator when the field of vision is located in the near range.

The actuator 6 runs around a free center in a ring-shaped manner and thus does not interfere with the field of view.

Except for the actuator 6, the self-accommodating lens can be formed in the same way as the above-described exemplary embodiments.

The implementation of the control elements, which are present for an accommodating lens, was improved further by means of the invention.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations and broad equivalent arrangements that are included within the spirit and scope of the following claims.

LIST OF REFERENCE NUMERALS 1 self-accommodating lens
2 lens body
3 maximum opening iris
4 controller
5 patch antenna
6 actuator
7 center point/optical axis
8 thin film actuator/coil
9 free region
10 antenna
11 reflector
12 patch array
13 substrate
14 signal lobe
15 flexible substrate
16 electrode
17 hollow space
18 eye

What is claimed is:

1. A self-accommodating lens, comprising:
a lens body configured to be placed onto or into an eye of a patient;
an actuator configured to modify a curvature of the lens body;
an antenna, which emits a directional radio signal in a signal lobe having a beam width of 30°; and
a controller operatively connected to the antenna and to the actuator,
wherein the controller is configured to detect a signal intensity of a received direction radio signal emitted by an adjacent lens and to calculate a control signal for the actuator based on the signal intensity of the received direction radio signal.

2. The self-accommodating lens according to claim 1, wherein the antenna is formed as patch antenna.

3. The self-accommodating lens according to claim 2, wherein the antenna is formed as a patch array.

4. The self-accommodating lens according to claim 3, wherein the antenna is formed as a curved patch array.

5. A set comprising two self-accommodating lenses, at least one of the two self-accommodating lenses being the self-accommodating lens according to claim 1.

6. The self-accommodating lens according to claim 1, wherein the controller is configured to
not generate a control signal if the signal intensity of the received direction radio signal is indicative of an angle of an optical axis of the lens being less than a first threshold, and to
generate a first control signal if the signal intensity of the received direction radio signal is indicative of the angle of the optical axis of the lens being between the first threshold and a second threshold, and to generate a second control signal if the signal intensity of the received direction radio signal is indicative of the angle of the optical axis of the lens being above the second threshold.

7. The self-accommodating lens according to claim 6, wherein the first threshold is 5 degrees, and the second threshold is 10 degrees.

8. The self-accommodating lens according to claim 6, wherein the first control signal causes a diopter value of the self-accommodating lens to increase by 2.5, and wherein the second control signal causes the diopter value of the self-accommodating lens to increase by 5.

\* \* \* \* \*